United States Patent
Duckert et al.

(10) Patent No.: US 7,711,582 B2
(45) Date of Patent: May 4, 2010

(54) REMOTE HEALTH APPLICATION FOR THE OPTIMIZATION OF REMOTE SITE VISIT FREQUENCY

(75) Inventors: David W. Duckert, Menomonee Falls, WI (US); Bruce A. Friedman, Tampa, FL (US)

(73) Assignee: General Electric Company, Schenectady, NY (US)

( * ) Notice: Subject to any disclaimer, the term of this patent is extended or adjusted under 35 U.S.C. 154(b) by 933 days.

(21) Appl. No.: 11/279,935

(22) Filed: Apr. 17, 2006

(65) Prior Publication Data

US 2007/0255596 A1 Nov. 1, 2007

(51) Int. Cl.
*G06Q 10/00* (2006.01)

(52) U.S. Cl. ............... 705/3; 705/2; 600/300; 600/301

(58) Field of Classification Search .......... 705/2–4; 600/300–301
See application file for complete search history.

(56) References Cited

U.S. PATENT DOCUMENTS

| | | | | |
|---|---|---|---|---|
| 5,361,327 | A * | 11/1994 | Takahashi | 706/22 |
| 5,455,891 | A * | 10/1995 | Hirotsu et al. | 706/25 |
| 5,485,908 | A * | 1/1996 | Wang et al. | 194/317 |
| 7,609,150 | B2 * | 10/2009 | Wheatley et al. | 340/436 |
| 2002/0082865 | A1 | 6/2002 | Bianco et al. | |
| 2002/0087116 | A1 * | 7/2002 | Hartlaub | 604/65 |
| 2003/0033261 | A1 * | 2/2003 | Knegendorf | 705/400 |
| 2003/0084014 | A1 * | 5/2003 | Sohrabi et al. | 706/20 |
| 2004/0153440 | A1 * | 8/2004 | Halevy et al. | 707/3 |
| 2004/0167805 | A1 * | 8/2004 | Landsman et al. | 705/3 |
| 2004/0249676 | A1 | 12/2004 | Marshall et al. | |
| 2005/0131740 | A1 | 6/2005 | Massenzio et al. | |
| 2006/0136267 | A1 | 6/2006 | Brackett et al. | |
| 2007/0206755 | A1 * | 9/2007 | Vizaei | 379/201.02 |
| 2009/0106051 | A1 * | 4/2009 | Albro et al. | 705/3 |

OTHER PUBLICATIONS

"Chronic Disease Coordinated Care Planning: Flexible, Task-Centered Decision Support", Warren et al., Proceedings of the 32nd Hawaii Int'l Conf. on System Sciences—1999 (0-7695-001-3/990, pp. 1-12.

* cited by examiner

*Primary Examiner*—Vivek D Koppikar
(74) *Attorney, Agent, or Firm*—Andrus, Sceales, Starke & Sawall, LLP

(57) ABSTRACT

A system and method for the optimization of scheduling visits by a clinician to a plurality of remotely located patients. A plurality of predefined or clinician specified risk factors are combined with patient data with a home visit interval algorithm to specify a visit interval for each patient. This interval is used with a calendar with other information regarding past and future scheduled visits to determine the optimal date for the next visit to the patient by the clinician. The patient risk factors may be weighted to place more emphasis on specific factors, thus allowing for the tailoring of the system to meet the needs of an individual patient.

21 Claims, 2 Drawing Sheets

REMOTE HEALTH APPLICATION FOR THE OPTIMIZATION OF REMOTE SITE VISIT FREQUENCY

FIELD OF THE INVENTION

The present invention relates to the field of health care management systems. More specifically, the invention relates to a system for monitoring and managing the need for a clinician to visit a patient at a remote site.

BACKGROUND OF THE INVENTION

The rising cost of health care is of increasing concern to many. One way to reduce the cost of medical treatment is to reduce the number of days that are spent in the hospital as there is a large fundamental cost that is associated with each night spent in a hospital bed. As a result, there has been a continued push towards home centered and/or remote offsite patient treatment and/or convalescence. This increased push for remote patient care presents its own significant challenges for health care providers due to the lack of personal contact that clinicians have with patients that are located at remote sites. While mobile communication systems and telemonitoring have greatly increased the quality of the care provided to patients that are being treated or are recovering at a location remote from the hospital, clinicians have found it useful to augment the care provided via these systems with remote site visits by the clinicians to check up on the patients in person. In-person visits may be particularly necessary where the remotely located patient experiences difficulty in making regularly scheduled visits to a medical care facility, perhaps due to mobility issues that are part of the patient's ailments or perhaps due to a lack of available transportation options or the patient's remote location.

Many types of patient conditions may lead to a situation where it is desirable for a clinician to periodically check up on the patient's condition with a visit to the remote site at which the patient is located. The patient's condition may be that of a chronic disease such as chronic obstructive pulmonary disease (COPD), congestive heart failure (CHF) or another manageable chronic disease such as diabetes. Other times, a patient's physical or mental disability may make periodic remote site checkups by the clinician desirable as well.

It is known in the field that in-person interaction between the clinician and the patient is advantageous to the treatment and/or recovery of the patient from his affliction. These clinician/patient interactions do, however, experience a diminishing rate of return as the interactions substantially increase in number. Therefore, in a system where a relatively smaller number of clinicians must provide care to a relatively larger number of patients, the interest of efficiency requires that clinician visits to remotely located patients must be scheduled in such a way as to maximize the quality of care given to each individual patient while minimizing the amount of time spent with that patient out of the pool of clinician time devoted to the treatment of all patients.

Various devices, systems, and methods have been developed to alleviate some of the above-noted issues regarding patient health care. In particular, U.S. Patent Application No. 2005/0131740 to Massenzio et al. describes a system and method for controlling home health care services. The '740 application discloses a system by which the efficiency of remote care is improved by the transmission of remote patient alarm conditions. Health care providers are able to maximize their efficiency in providing emergency care to multiple remotely located patients by tracking the patient's locations using GPS and triaging the patients based upon the specific emergency conditions. However, this application does not address the scheduling and provision of non-emergency clinician visits or checkups.

U.S. Patent Application No. 2004/0249676 is directed to a system for the automatic scheduling of patients on waiting lists to receive medical treatments such as elective surgery, diagnostic services, clinic services and endoscopies. This system uses a calculated urgency score to calculate the target date for the patient's procedure based upon patient recorded physiological data and a ranked triage of patient procedure need. This system is limited in its application in that it only projects a date or schedule for a specific procedure and is not directed toward the scheduling of recurring clinician checkups or visits. Additionally, this disclosure does not contemplate the use of a wide variety of patient diagnostic data, but rather is limited to the evaluation of patient physiological data.

Therefore, it is desirable in the field of the provision of care to remotely located patients to provide an automated system by which clinician visits to remotely located patients are scheduled in an economical fashion.

Furthermore, it is desirable that the scheduling be based on a wide variety of diagnostic parameters such as clinician-observed or so-called "soft" parameters.

In a further embodiment of the present invention, it is desirable that the management system take into account other related data such as already scheduled clinician visits, patient requests for additional or fewer clinician visits, or remote patient locations with respect to the locations of other remotely located patients.

SUMMARY OF THE INVENTION

The present invention provides a system and method by which a plurality of patient risk factors are considered in determining the scheduling of a clinician visit to a remotely located patient. This system utilizes a variety of risk factors that are combined in a home visit interval algorithm to produce a determination of the date for the next home visit.

In an embodiment of the present invention, the risk factors comprise a variety of parameters including, but not limited to, physiological parameters, clinician-observed parameters, patient-initiated parameters, and patient history parameters.

In a still further embodiment of the present invention, each risk factor has an associated weight that may be developed by "learning" using a neural network or fuzzy logic methods or other type of weight optimization algorithm or technique.

In a still further embodiment of the present invention, the risk factors may trigger an alarm condition whereby emergency and/or immediate clinician intervention may be necessary. The system includes a means for notifying the clinician of this alarm condition.

BRIEF DESCRIPTION OF THE DRAWINGS

The drawings illustrate the best mode presently contemplated of carrying out the invention. In the drawings.

DETAILED DESCRIPTION OF THE INVENTION

Figure 1:
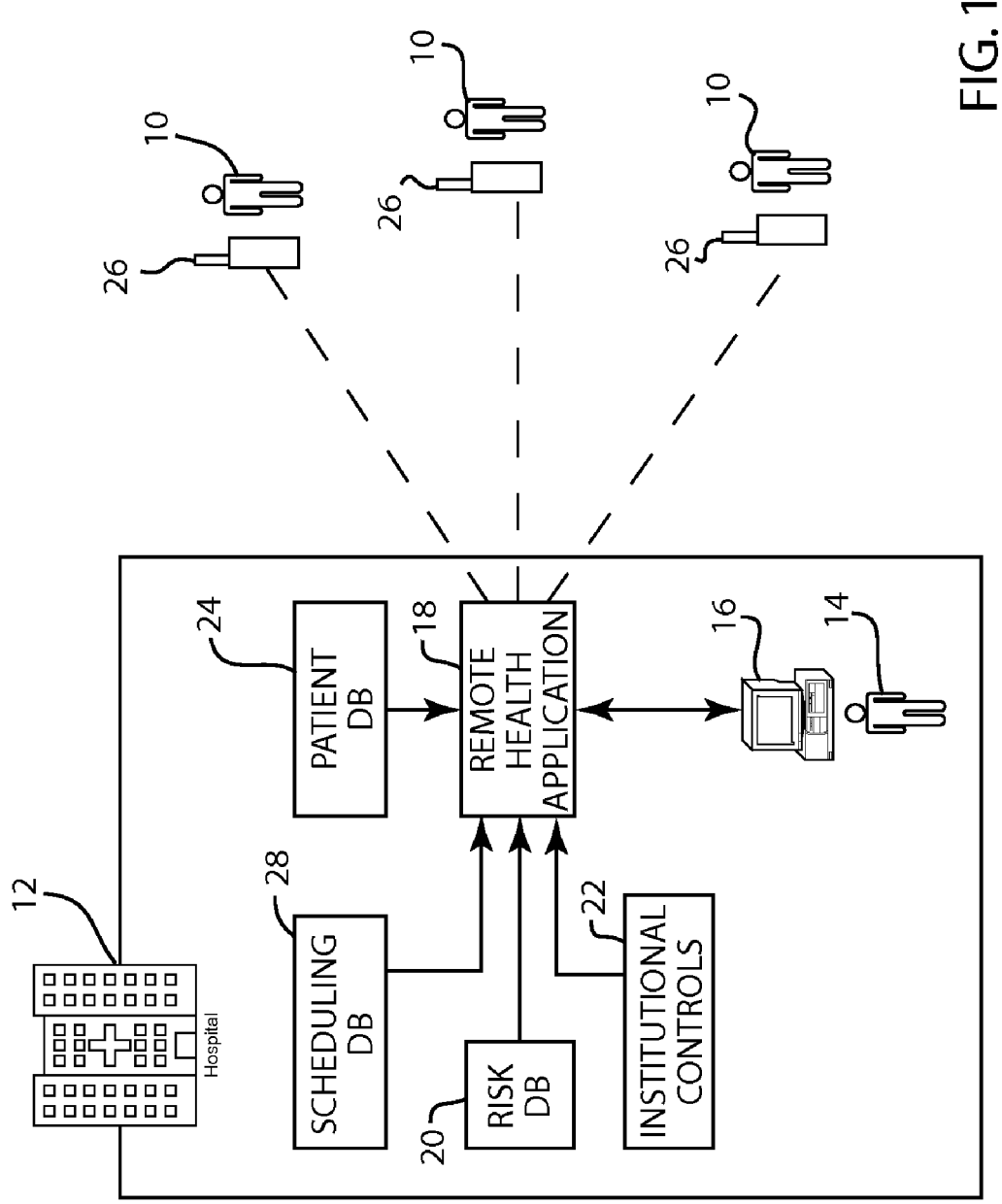
FIG. 1 is a schematic diagram of the operation of the system of the present invention.

FIG. 1 depicts a schematic diagram of a situation in which an embodiment of the present invention may be utilized. In FIG. 1, a plurality of remotely located patients 10 are each at a location that is different from each other and all are remote from the clinical institution 12. The clinical institution 12 may be a regional hospital, local clinic, or any other provider of patient care. An on-line clinician 14 at a computer work station 16 within the clinical institution 12 monitors the scheduling of visits by a clinician (not depicted) to each remotely located patient 10. The remote health application 18 of the present invention receives information from a variety of sources, such as patient data, risk factors, and scheduling information, for determining the proper schedule for clinician visits to the remotely located patients 10.

The remote health application 18 uses risk factors from a risk database 20 and other institutionally determined controls 22 for operating the remote health application 18. The risk factors 20 and institutional controls 22 may be supplemented or modified by the on-line clinician 14 to more specifically tailor the remote health application 18 to a specific patient depending upon that patient's diagnosis and treatment schedule. The remote health application 18 will use patient data provided to it via a patient database 24 as well as data received from a communications device 26 that is associated with each of the remotely located patients 10. The communications device 26 may comprise but is not herein limited to internet communication, cellular communication, WIFI communication, or any other means with which the patient 10 may transmit a data or communications signal from the communications device 26 to the remote health application 18 and on-line clinician 14.

The remote health application 18, as will be described further herein, uses the data received from the patient database 24 as well as the data received directly from the patient 10 with the risk factors from the risk factor database 20 to determine the need for a visit by a clinician to the remotely located patient. Scheduling database 28 provides information regarding each patient's most recent clinician visit and next scheduled clinician visit to the remote health application 18. This allows for the remote visit schedule to be modified based upon the determined patient need for a clinician visit in light of already scheduled out-patient visits.

Figure 2:
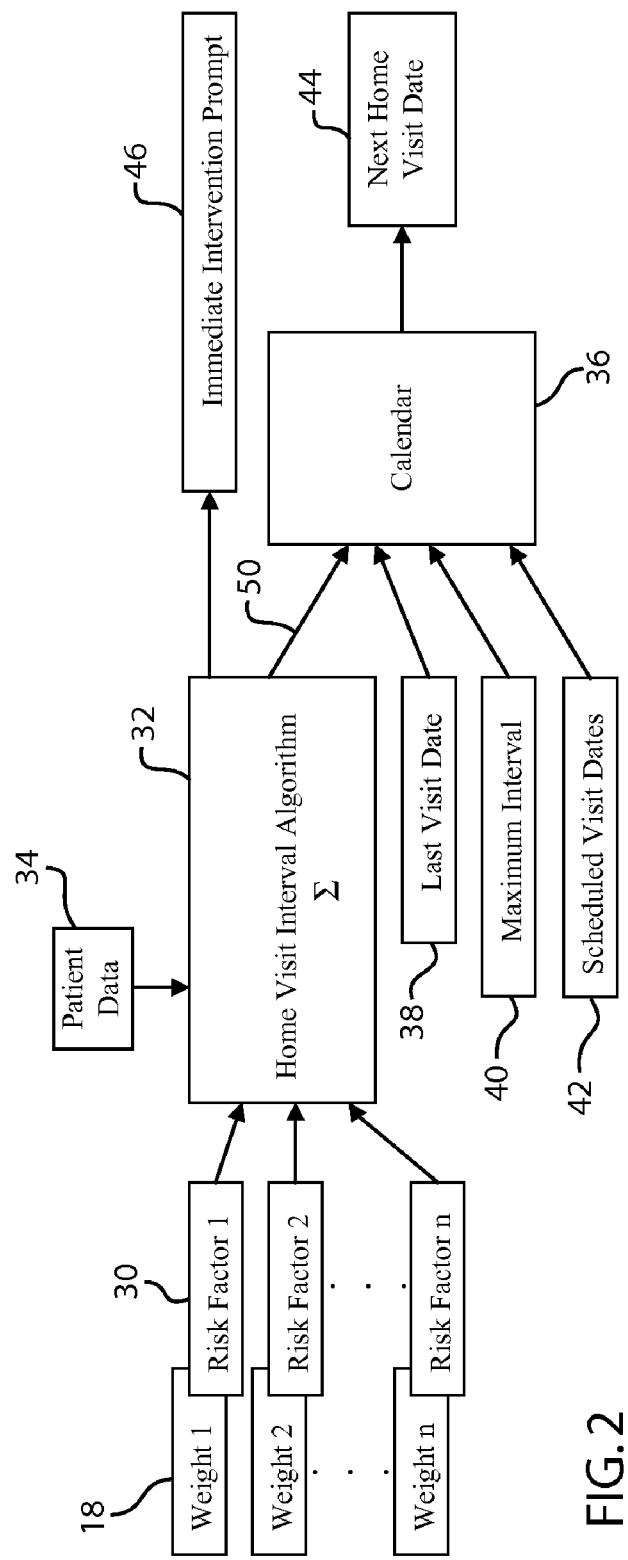
FIG. 2 is a schematic diagram of the operation of the remote health application of the present invention.

FIG. 2 is a schematic diagram of the operation of the remote health application 18 of FIG. 1. As depicted in FIG. 2, a plurality of risk factors 30 are sent to home visit interval algorithm 32. These risk factors 30 are used to analyze the patient data 34 that may be received from the variety of sources depicted in FIG. 1, such as the scheduling database 28, the patient information database 24, and/or the patient communications device 26. The home visit interval algorithm 32 determines the current proper interval between home visits for that patient. The home visit interval algorithm 32 also determines whether the home visit interval 50 has been increasing over time, thereby showing an improvement in overall patient health, or whether the home visit interval 50 is decreasing over time, thereby indicating a general decline in overall patient health.

The home visit interval 50 is sent to the scheduling calendar 36 where the interval 50 is compared to additional scheduling information such as the last visit date 38, a maximum interval duration that may apply to this patient's care 40, or any already scheduled visit dates for this patient 42. The last visit date 38 may comprise any clinician visits to the patient, but may also comprise any visits by the patient to the clinical institution 12. The calendar 36 uses this information with the home visit interval 50 to set the date of the next home visit 44.

The risk factors 30 that are supplied to the home visit interval algorithm 32 may comprise rules to interpret a variety of patient data that may be supplied to the algorithm 32 to determine the home visit interval 50. The risk factors 30 may interpret patient data that is dynamic or static, continuous or discrete, and objective or subjective. The patient data 34 interpreted may compromise data from the patient database 24, institutional controls 22, and data from the scheduling database 28. An exemplary listing of data that may be provided by the patient database 24 could include the patient's compliance level and/or compliance history with prescribed medications and treatments, the patient's medical history including current disease level and/or disease progression, the patient's psychological profile, and information pertaining to the number of people living with the patient at the remote location. Institutional controls 22 that may be used in determining the home visit interval 50 may be information regarding other remote patients in the local area and the dates of their next clinician visits, the GPS location of clinicians available to provide remote care, the existence of a contractual or regulatory requirement for visit frequency, or other institutionally determined clinical guidelines or pathways. Finally, relevant data that may be included from the scheduling database 28 may include the date of the last visit with a health care provider, length of time since the most recent home health visit or doctor's appointment, any appointments for physical specimen collection, any scheduled clinical events, the next scheduled doctor's appointment, or the next scheduled home health visit.

The risk factors 30 may also include factors relating to data that may be received from the communications device 26, including data collected from the patient regarding transduced physiological parameters from the patient or patient initiated communications. Factors that may be received via the communications device 26 from the patient may include, but are not limited to: the patient's activity level, physiological data recorded by a telemetry system, voice analysis data, gait analysis data, a recorded log of patient visitors, the patient's answer to self-assessment questions, requests for an appointment by the patient, clinician, or doctor, and patient environmental data, such as the ambient temperature or relative humidity of the patient's home or remote location.

The home visit interval algorithm 32 combines the patient data 34 with the risk factors 30 to determine the proper interval between remote care clinician visits to the patient. In an embodiment of the present invention, each risk factor may include an associated weight whereby specific risk factors are given more consideration by the home visit interval algorithm than other risk factors. The patient data 34 and risk factors 30 may be combined in the form of if/then statements to produce the home visit interval result. The following examples of output statements are designed to be exemplary and not limiting upon the present invention:

1) If a patient who had previously been very timely about collecting vital sign measurements suddenly stops taking his/her physiological measurements, then that patient becomes higher risk and in an embodiment of the present invention, may initiate some form of immediate intervention alarm.
2) If a person has other household members who participate in the care of that patient, then that patient has lower risk and the interval between home care visits can be increased.
3) If a patient's activity level is decreasing, then that patient becomes higher risk and the time to the next scheduled home visit is reduced.
4) If a patient has a doctor's office visit scheduled in the near future, then that patient has lower risk and the next home visit date is delayed.

Logical output statements such as the preceding exemplary statements are used by the home visit interval algorithm to determine a home visit interval 50 that is sent to the scheduling calendar 36. In an embodiment of the present invention, the home visit interval 50 may be combined with other calendar data such as the patient's most recent clinician visit date 38, a maximum visit interval 40 which may be a contractually, institutionally, professionally, or legally defined maximum visit interval, or other patient visit dates 42 already scheduled in the calendar 36. The calculated home visit interval 50 is compared to any maximum visit interval 40 to determine if the interval should be modified to meet these constraints.

Next, the interval 50 is run from the most recent visit date 38 to determine the tentative next visit date. This tentative date is compared to any already scheduled visit dates 42 to create optimization of patient visits. Once the home visit interval 50 has been processed through the calendar 36, the next home visit date 44 has been determined. The patient may then be notified of this next home visit date 44 via the communications device 26 or other notification means.

In an embodiment of the present invention, the associated weights for each risk factor may start as a default value, but may be modified later by a clinician to specifically tailor the home visit interval algorithm to the particular needs of an individual patient, or the associated weight of each risk factor may be developed by "learning" using a neural network or fuzzy logic method. This learning of the weight values for a risk factor may be done by observing patient data or by the entering of additional patient data by a clinician to form a pool of patient data from which the associated weights may be learned.

In a still further embodiment of the present invention, the detection of certain risk factors of specified weights may result in the triggering of an alarm condition which would result in an intervention prompt 46 to be displayed to the clinician. This intervention prompt 46 would notify a clinician of the emergency situation and as such enable the clinician to respond to the emergency situation accordingly.

This written description uses examples to disclose the invention, including the best mode, and also to enable any person skilled in the art to make and use the invention. The patentable scope of the invention is defined by the claims and may include other examples that occur to those skilled in the art. Such other examples are intended to be within the scope of the claims if they have structural elements that do not differ from the literal language of the claims, or if they include equivalent structural elements of insubstantial difference from the literal language of the claims.

Various alternatives and embodiments are contemplated as being with in the scope of the following claims, particularly pointing out and distinctly claiming the subject matter regarded as the invention.

We claim:

1. A system for scheduling clinical visits to a remotely located patient, the system comprising:
   a plurality of patient risk factors stored on a risk factor database, the plurality of patient risk factors each comprising a default value wherein the default value is a weight that enables the emphasis of some patient risk factors over others in determining the visit interval;
   patient data stored on a patient database;
   a visit interval algorithm operating on a computer processor connected to the risk factor database and the patient database, the visit interval algorithm upon execution by the computer processor derives a visit interval from the plurality of patient risk factors and the patient data; and
   a calendar operating on the computer processor, the calendar comprising a previous patient visit and the calendar schedules a patient visit for a date that is the visit interval from the previous patient visit;
   wherein the default values are modified over time using fuzzy logic or a neural network, in response to collected patient data.

2. The system of claim 1 wherein the visit date information further comprises any scheduled contact with a healthcare provider involved with the patient's treatment.

3. The system of claim 1 wherein the visit interval algorithm comprises institutionally defined controls.

4. The system of claim 3 wherein the institutionally defined controls are maximum visit intervals.

5. A system for real-time scheduling of clinician visits to a patient receiving care at a remote location, the system comprising:
   a communications device associated with the patient, the communications device transmitting patient physiological data from the patient to a processor in real time;
   a plurality of risk factors stored in a risk factor database connected to the processor, each of the plurality of risk factors comprising a default value wherein the default value is a weight that enables the emphasis of some patient risk factors over others;
   a patient database storing patient medical history information connected to the processor;
   a visit interval algorithm stored on a computer readable medium and executed by the processor, the visit interval algorithm applying the patient physiological data and the patient medical history information to the plurality of risk factors to determine a visit interval; and
   a calendar comprising a past patient visit date, the calendar receives the visit interval from the processor and schedules a patient visit for a date that is the visit interval from the past patient visit date;
   wherein the default values are modified over time based upon the patient physiological data using fuzzy logic or a neural network.

6. A method of optimizing the care provided by a clinician to a plurality of remotely located patients with treatment and care needs, the method comprising the steps of:
   providing each patient with an associated communications device;
   transmitting patient data via the communications device to a computer workstation comprising a processor;
   operating the processor to execute a remote health application stored on a computer readable medium, which upon execution performs the steps of:
      comparing at least one patient risk factor, the at least one patient risk factor having a default value, to the patient data to determine a patient visit interval;
      deriving a patient visit date by adding the patient visit interval to a past patient visit date;
      scheduling the patient visit date;
   notifying the patient of the scheduled patient visit date via the communications device; and
      modifying the default value of the at least one patient risk factor in response to the patient data using fuzzy logic or a neural network;
      wherein the default value is a weight that enables the emphasis of some patient risk factors over others in determining the patient visit interval.

7. The method of claim 6 wherein the patient data transmitted via the communications device comprises linguistic communication and physiological patient data.

8. The method of claim 7 wherein the linguistic communication provides the clinician with qualitative information regarding the patient's condition, the patient data comprising the qualitative information.

9. The system of claim 1 wherein the patient visit scheduled by the calendar replaces a previously scheduled future patient visit.

10. The system of claim 9 further comprising a communication device associated with the patient, the communication device transmits measured patient data to the processor.

11. The system of claim 10 wherein the processor produces an indication of the scheduled patient visit and the communication device further receives the indication of the scheduled patient visit.

12. The system of claim 10 wherein upon the communication device transmitting the measured patient data to the processor, the visit interval algorithm calculates a new visit interval and the calendar replaces the future patient visit with a new patient visit based on the new visit interval.

13. The system of claim 5 wherein upon the communications device transmitting patient data to the processor, the visit interval algorithm calculates a new visit interval and the calendar replaces a future patient visit with a new patient visit based on the new visit interval.

14. The method of claim 6 further comprising operating the processor to update the patient visit interval and updating the scheduled patient visit date each time that patient data is transmitted to the processor from the communications device.

15. The method of claim 6 further adjusting a scheduled visit date of a first patient to a scheduled visit date of a second patient based upon the geographical proximity of the first patient to the second patient.

16. The system of claim 1 wherein the default values are modified over time using fuzzy logic.

17. The system of claim 1 wherein the default values are modified over time using a neural network.

18. The system of claim 5 wherein the default values are modified over time using fuzzy logic.

19. The system of claim 5 wherein the default values are modified over time using a neural network.

20. The method of claim 6 wherein the step of modifying uses fuzzy logic.

21. The method of claim 6 wherein the step of modifying uses a neural network.

* * * * *